(12) United States Patent
Riesinger

(10) Patent No.: US 7,775,998 B2
(45) Date of Patent: Aug. 17, 2010

(54) MULTI-COMPONENT DRESSING FOR TREATING WOUNDS OF THE HUMAN OR ANIMAL BODY USING A REDUCED PRESSURE

(76) Inventor: Birgit Riesinger, Zum Holtkamp 8, 48348 Ostbevern (DE)

( * ) Notice: Subject to any disclaimer, the term of this patent is extended or adjusted under 35 U.S.C. 154(b) by 0 days.

(21) Appl. No.: 11/666,848

(22) PCT Filed: Nov. 2, 2005

(86) PCT No.: PCT/EP2005/011701
§ 371 (c)(1),
(2), (4) Date: Jul. 5, 2007

(87) PCT Pub. No.: WO2006/048246
PCT Pub. Date: May 11, 2006

(65) Prior Publication Data
US 2008/0004559 A1   Jan. 3, 2008

(51) Int. Cl.
*A61F 5/00* (2006.01)
*A61F 13/00* (2006.01)
(52) U.S. Cl. .............................. 602/2; 602/48; 604/289; 604/290
(58) Field of Classification Search .................. 602/43, 602/46, 48, 2; 604/289, 290, 304–308
See application file for complete search history.

(56) References Cited

U.S. PATENT DOCUMENTS

| | | | |
|---|---|---|---|
| 3,111,948 A | 11/1963 | Burgeni | |
| 3,364,931 A | 1/1968 | Hirsch | |
| 3,871,376 A | 3/1975 | Kozak | |
| 3,872,862 A | 3/1975 | Hume | |
| 4,382,441 A | 5/1983 | Svedman | |
| 4,592,750 A | 6/1986 | Kay | |
| 4,969,880 A * | 11/1990 | Zamierowski | ............ 604/305 |
| 5,086,763 A | 2/1992 | Hathman | |
| 5,476,664 A | 12/1995 | Robinson | |

(Continued)

FOREIGN PATENT DOCUMENTS

DE        33446        10/1984

(Continued)

OTHER PUBLICATIONS

International Search Report (WO2008/040681 dated Feb. 19, 2008).

(Continued)

*Primary Examiner*—Kim M Lewis
(74) *Attorney, Agent, or Firm*—Occhiuti Rohlicek & Tsao LLP

(57) ABSTRACT

A multi-component dressing (100) for treating wounds of the human or animal body, using a reduced pressure, comprising a wound-covering element (4) for mounting the dressing (100) at the surface of the skin and the mucous membrane having at least one connecting site (5) through which material in the wound space (10) can be evacuated. The multi-component dressing has super-absorbing polymers, the absorbed wound secretions remaining bound to polymers in the wound space until the latter are removed from the wound space and the polymers, due to their binding capacity, supporting reciprocal synergies with the sub-atmospheric pressures. Wound exudate, promoted by the reduced pressure, is also stored and controlled by polymerized granulates.

10 Claims, 2 Drawing Sheets

U.S. PATENT DOCUMENTS

| | | | |
|---|---|---|---|
| 5,540,922 | A | 7/1996 | Fabo |
| 5,549,584 | A | 8/1996 | Gross |
| 5,636,643 | A | 6/1997 | Argenta et al. |
| 6,071,267 | A | 6/2000 | Zamierowski |
| 6,174,306 | B1 | 1/2001 | Fleischmann |
| 6,333,093 | B1 | 12/2001 | Burrell |
| 6,398,767 | B1 | 6/2002 | Fleischmann |
| 6,626,891 | B2 | 9/2003 | Ohmstede |
| 6,966,901 | B2 | 11/2005 | Leisner |
| 7,048,706 | B2 * | 5/2006 | Cea .............................. 602/26 |
| 2002/0065494 | A1 | 5/2002 | Lockwood et al. |
| 2004/0054338 | A1 | 3/2004 | Bybordi |
| 2006/0009744 | A1 | 1/2006 | Erdman |
| 2008/0009812 | A1 | 1/2008 | Riesinger |
| 2008/0119802 | A1 | 5/2008 | Riesinger |

FOREIGN PATENT DOCUMENTS

| | | | |
|---|---|---|---|
| DE | 3850798 | | 10/1988 |
| DE | 100 59 439 | A1 | 11/2000 |
| DE | 10059439 | A1 * | 8/2001 |
| EP | 0762860 | | 12/1997 |
| EP | 1 177 781 | A2 | 7/2000 |
| EP | 1129734 | | 9/2001 |
| GB | 2272645 | | 5/1994 |
| WO | WO83/02054 | | 6/1983 |
| WO | WO96/05873 | | 2/1996 |
| WO | WO99/01173 | | 1/1999 |
| WO | WO 01/10363 | A1 | 2/2001 |
| WO | WO01/89431 | | 11/2001 |
| WO | WO03/094813 | | 11/2003 |
| WO | WO2005/123170 | | 12/2005 |
| WO | WO2006/048240 | | 5/2006 |
| WO | WO2006/056294 | | 6/2006 |
| WO | WO2008/040681 | | 4/2008 |

OTHER PUBLICATIONS

International Preliminary Report on Patentability (WO2008/040681 dated Apr. 7, 2009).

International Search Report (WO2006/048240 mailed Mar. 9, 2006).

International Preliminary Report on Patentability (WO2006/048240 dated May 8, 2007).

International Search Report (WO2006/048246 dated Jun. 3, 2006).

International Preliminary Report on Patentability (WO2006/048246 dated May 22, 2007).

International Search Report (WO2006/056294 dated Apr. 10, 2006).

International Preliminary Report on Patentability (WO2006/056294 dated May 30, 2007).

* cited by examiner

MULTI-COMPONENT DRESSING FOR TREATING WOUNDS OF THE HUMAN OR ANIMAL BODY USING A REDUCED PRESSURE

BACKGROUND OF THE INVENTION

The invention relates to a multi-component dressing for treating wounds of the human or animal body using a reduced pressure, having a wound-covering element for mounting the dressing at the surface of the skin and mucous membrane and at least one connecting site, which is in contact with the wound space and over which the materials, in the wound space, can be evacuated.

Such a multi-component dressing is known from U.S. Pat. No. 5,636,643. It is a disadvantage of the known multi-component dressing that the wound secretion can be withdrawn from the region of the wound exclusively over a hose line.

SUMMARY OF THE INVENTION

It is an object of the invention to conceive a novel multi-component dressing, for which the wound secretions can remain in the region of the wound without these wound secretions being able to develop their harmful properties in the region of the wound.

This objective is accomplished by a multi-component dressing of the type named above, which is characterized in that this dressing has super-absorbing polymers, the absorbed wound secretions remaining bound to the polymers in the wound space, until the latter are removed from the wound space, the polymers, due to their binding capacity, supporting reciprocal synergies with the sub-atmospheric pressures.

All known polymers, preferably however those from the group of sodium polyacrylates, may be selected as polymers.

The multi-component dressing may be provided with at least one enveloping absorption body, which has at least one layer of a textile section, which is interspersed with super-absorbing particles.

The absorption body may be surrounded by a liquid-permeable envelope, which, in turn, has pores, the size of which essentially does not exceed that of the super-absorbing particles. The reduced pressure, generated on the outside, is passed over a hose line or optionally over a suction head into the wound space, where it supports desired synergies with the polymers.

For a full understanding of the present invention, reference should now be made to the following detailed description of the preferred embodiments of the invention as illustrated in the accompanying drawings.

DESCRIPTION OF THE PREFERRED EMBODIMENT

Figure 1A:
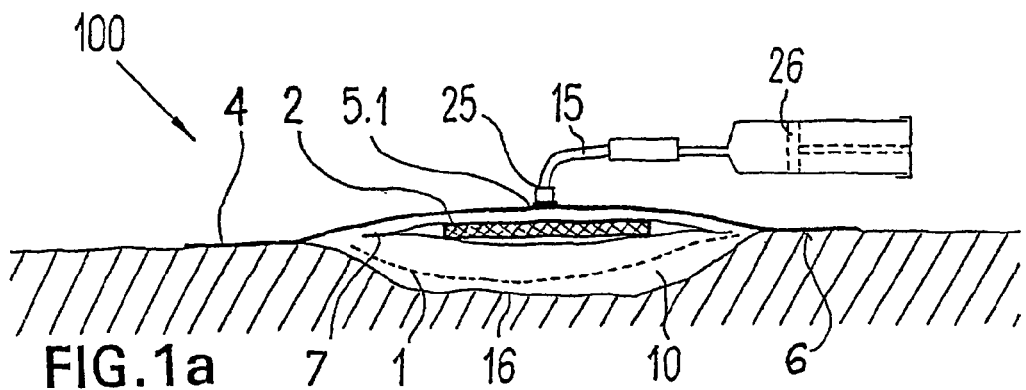
FIGS. 1a to 1d show a multi-component dressing, glued to the skin of the patient about a wound, in a diagrammatic section.
Figure 1B:
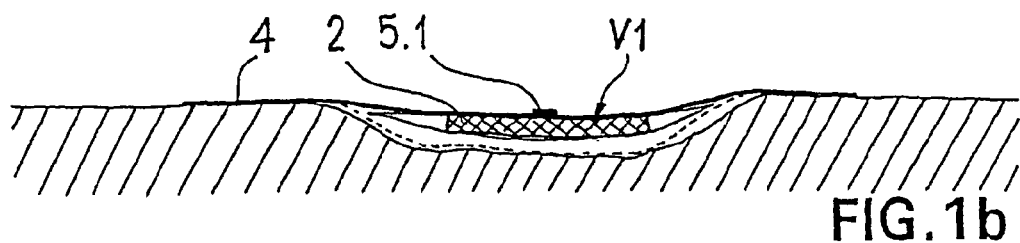
Figure 1C:
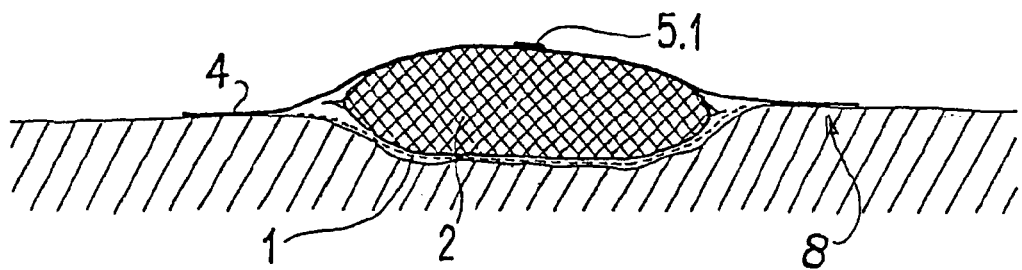

FIGS. 1a to 1d show a multi-component dressing 100 for treating wounds using a reduced pressure, consisting of a film-like wound-covering element 4, an optional film element 1, which is compatible with the mucous membrane and, lying between these, an absorption body 2. In a plan view of its flat side, the multi-component dressing is somewhat rectangular and has rounded corners (not shown). The wound-covering element 4, consisting of a liquid-impermeable, transparent film, is relatively stiff, that is, it does not shrink when not in use and when in contact with the body of the patient. At its periphery 8, the wound-covering element 4 is provided with an adhesive surface 6 for gluing the multi-component dressing to the skin of the patient.

The absorption body 2 consists of a layer of a nonwoven textile material, which comprises cellulose fibers and is interspersed with super-absorbing particles (Super-Absorbing-Polymers, SAP), in the present case, with a copolymer of sodium acrylate and acrylic acid. In addition, the absorption body 2 is enriched with nanocrystalline, silver-containing substances, which have a microbiocidal effect. The cellulose fibers act as an interim storage system for the liquid quantities, which are acted upon spontaneously, and as a sort of transporting means, with which the wound secretions reach the super-absorber.

The absorption body 2 is surrounded by a liquid-permeable, also textile envelope 11, which has been welded closed ultrasonically with a peripheral seam 7. As can be inferred particularly from FIG. 1d, the envelope has a peripheral overhang 30 of envelope material, which is located between the ultrasonic seam 7 and an outermost circumference 11 of the envelope. The overhang 30 is to prevent painful contact between the wound and the seam.

The film element 1, facing the wound, is made from a liquid-permeable, extremely thin, mucus membrane-compatible material. The film element 1 also contributes to protecting against contact with the ultrasonic seam 7.

Moreover, a connecting site 5.1 for evacuating gases and checking the vacuum is provided at the wound-covering element 4. According to FIGS. 1a to 1d and 2, the connecting site 5.1 is disposed approximately centrally. However, it may be located at any place on the wound-covering element, for example, in the vicinity of the periphery 8, as has been shown in FIGS. 2 and 3.

The absorption body 2, which is to be placed in the wound space 10, has an initial volume V1, which enlarges in the course of the absorption process and assumes a final volume V2, with which the wound space 10 and, with that, the wound defects can be filled during the swelling process.

Active substances, which affect the wound healing process 1, such as nanocrystalline silver particles, are applied to the material of the absorption body 2.

Figure 1D:
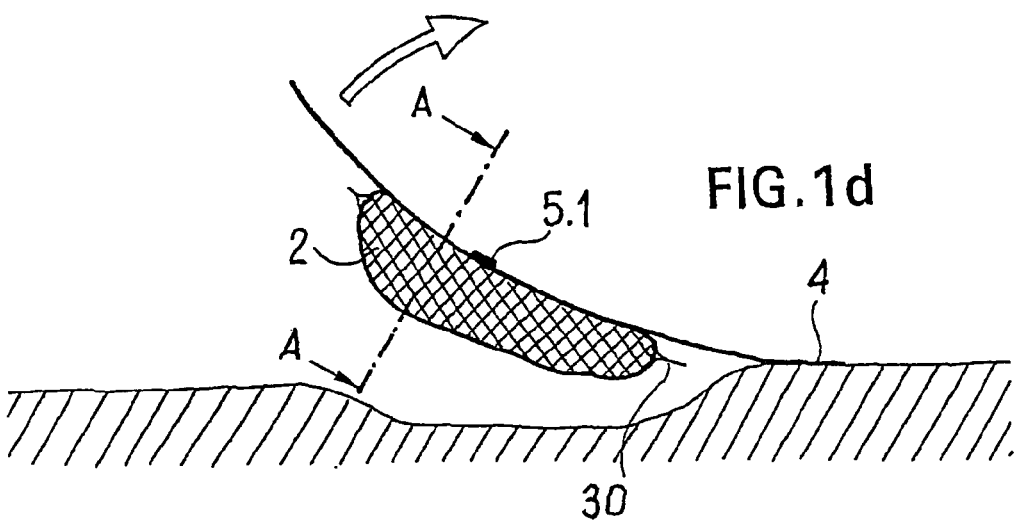

As shown by FIG. 1d, the absorption body 2 is glued over its whole surface to the wound-covering element 4, a periphery 8 at the wound-covering element being left free.

Figure 2:
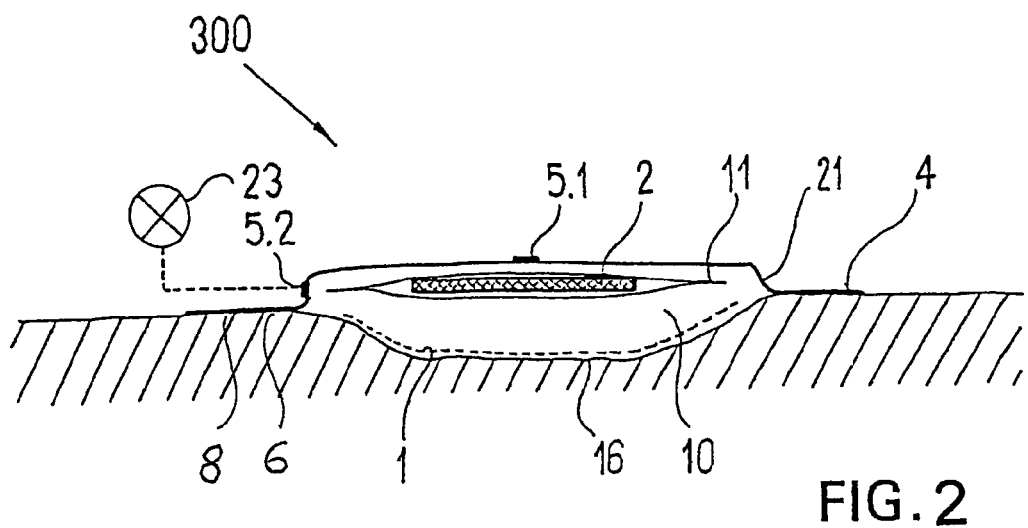
FIG. 2 shows a different embodiment of the multi-component dressing in a diagrammatic section.
Figure 3:
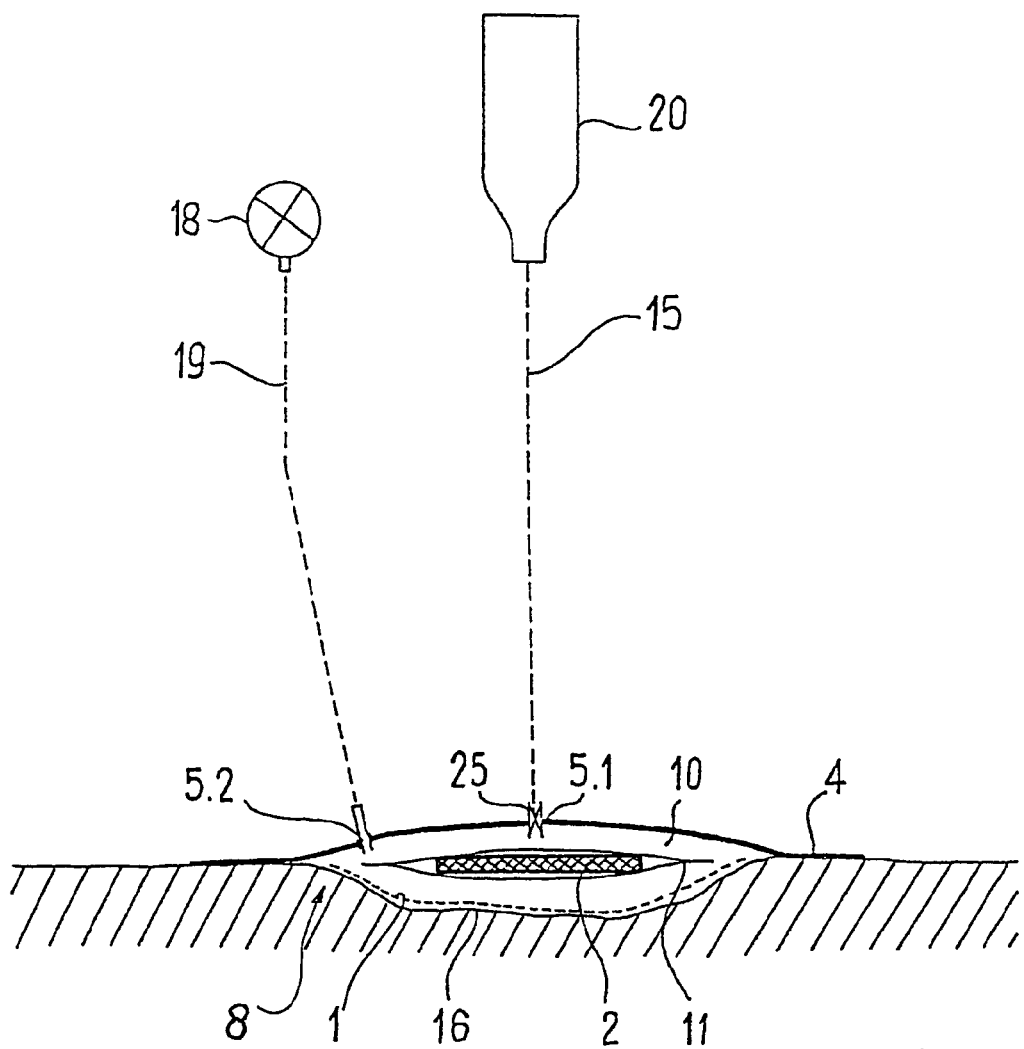
FIG. 3 shows the multi-component dressing of FIG. 1, however, with two connection sites, also in a diagrammatic section.

The multi-component dressing of FIG. 3 has two connecting sites 5.1, 5.2, of which the central one is for evacuating air and the second, lateral one for controlling the reduced pressure. A vacuum bottle 20 is connected over a hose line 15 to the central connecting site 5.1. On the other hand, an intermittent circuit 18 is connected, also over a connecting hose 19, with the lateral connecting site 5.2. FIG. 2 shows a similar dressing 300 having a controlled source of vacuum 23.

A chronic wound 16 is covered completely by gluing the multi-component dressing 100 of FIG. 1 to the skin of the patient. Previously, a pull-off film element (not shown), which exposes a peripheral adhesive surface 6 at the underside of the wound-covering element 4, was removed. To begin with, the mucous membrane-compatible film element 1 and then the flat absorption body 2 together with its envelope were placed carefully, with sterilized forceps, on the surface of the wound. Only then was the wound covering element 4 glued around the wound. By gluing the device to the skin, a wound space 10 is formed between the wound covering element 4 and the surface of the wound. A medical injection syringe 26 was connected over the aforementioned hose line 15 with the central connecting site 5.1, which is provided with a simple valve 25, as shown in FIG. 1a. Since the space 10 is sealed, the gases in the space can be evacuated with the aid of the injection syringe. This state is shown in FIG. 1b. The flat elements of the device lie in contact with the surface of the wound. The reduced pressure, measured meanwhile with the aid of a vacuum indicator (not shown), was about 100 mm Hg. For this purpose, the cylindrical casing surface of the injection syringe may be provided with an appropriate, experimentally defined, reduced pressure scale. The wound secretions, emerging from the wound, reach the absorption body 2 and bring about a slowly increasing compression beneath the wound-covering element 4. After wound secretions are aspired, the volume of the absorption body 2 increases greatly (see FIG. 1c). After use, the device 100 is removed carefully from the region of the wound by lifting it with the help of the forceps. If necessary, a new multi-component dressing can be glued to the wound.

There has thus been shown and described a novel multi-component dressing for treating wounds of the human or animal body using a reduced pressure which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A multi-component wound dressing for treating a wound on a human or animal body using a reduced pressure, said dressing comprising a wound covering element adapted to be applied to the surface of the skin to cover the wound, thereby forming a wound space, said wound covering element having at least one connector configured to connect to a pressure reducing device and through which only gases in the wound space can be evacuated, the improvement wherein the dressing has super-absorbing polymers which absorb the wound secretions in the wound space;

wherein the absorbed wound secretions, bound to the polymers, remain in the wound space until the polymers are removed; and wherein the polymers, due to their bonding capacity, support reciprocal synergies with the sub-atmospheric pressures.

2. The multi-component dressing of claim 1, wherein the polymers are selected from the group of sodium polyacrylates.

3. The multi-component dressing of claim 1, wherein the dressing has at least one enveloped absorption body with at least one layer of a textile section that is interspersed with supra-absorbing particles.

4. The multi-component dressing of claim 3, wherein the absorption body is enclosed in a liquid-permeable envelope, which has pores, the size of which essentially does not exceed that of the supra-absorbing particles.

5. The multi-component dressing of claim 4, wherein the absorption body, which is adapted to be placed in the wound space, has an initial volume (V1), which becomes enlarged in the course of the absorption process, and assumes a final volume (V2) with which the wound space and, with that, the respective wound material, can be filled during the swelling process.

6. The multi-component dressing of claim 4, wherein the layer, in plan view of its flat side, has a two-dimensional extent, which is 3% to 90% smaller than that of the envelope when placed flat.

7. The multi-component dressing of claim 3, wherein the material of the absorption body contains an active substance which has an effect on the wound healing process.

8. The multi-component dressing of claim 3, wherein the absorption body is glued to the wound covering element, a periphery being left free at the wound covering element.

9. The multi-component dressing of claim 7, wherein the active substance includes nanocrystalline silver particles.

10. A wound dressing for treating a wound on a human or animal body using a reduced pressure, said dressing comprising:

a wound covering element adapted to be applied to the surface of the skin to cover the wound, thereby forming a sealed wound space, said wound covering element having at least one connector configured to connect to a pressure reducing device and through which only gases in the wound space can be evacuated whereby a sub-atmospheric pressure environment is provided in the wound space, a pressure reducing device connected to the at least one connector; and super-absorbing polymers which absorb wound secretions in the wound space; wherein the absorbed wound secretions, bound to the polymers, remain in the wound space until the polymers are removed; and the polymers, due to their bonding capacity together with the sub-atmospheric pressure environment of the wound space, promote movement of secretions to the polymers.

* * * * *